US 6,389,368 B1

(12) United States Patent
Hampton

(10) Patent No.: US 6,389,368 B1
(45) Date of Patent: May 14, 2002

(54) BASKETBALL GOAL SENSOR FOR DETECTING SHOTS ATTEMPTED AND MADE

(76) Inventor: Randal R. Hampton, 2875 Taft Ave., Garner, IA (US) 50438

( * ) Notice: Subject to any disclaimer, the term of this patent is extended or adjusted under 35 U.S.C. 154(b) by 0 days.

(21) Appl. No.: 09/411,436

(22) Filed: Oct. 1, 1999

(51) Int. Cl.[7] .......................... G06F 17/18; A63B 63/08
(52) U.S. Cl. ....................... 702/179; 702/186; 473/479; 473/480
(58) Field of Search ......................... 702/150, 179–182, 702/186–188; 340/323 R; 473/433, 447, 479, 480; 700/91, 92; 348/157, 169

(56) References Cited

U.S. PATENT DOCUMENTS

| 4,858,920 A | | 8/1989 | Best | |
| 4,893,182 A | * | 1/1990 | Gautraud et al. | 473/101 |
| 4,904,981 A | | 2/1990 | Mele et al. | |
| 4,999,603 A | * | 3/1991 | Mele et al. | 340/323 R |
| 5,039,977 A | * | 8/1991 | Mele et al. | 700/92 |
| 5,171,009 A | | 12/1992 | Filewich et al. | |
| 5,294,913 A | | 3/1994 | Mower et al. | |
| 5,418,517 A | | 5/1995 | Matherne et al. | |
| 5,684,453 A | | 11/1997 | Welch | |
| 5,776,018 A | | 7/1998 | Simpson et al. | |
| 5,923,365 A | * | 7/1999 | Tamir et al. | 348/157 |

* cited by examiner

Primary Examiner—Bryan Bui
(74) Attorney, Agent, or Firm—Hovey, Williams, Timmons & Collins

(57) ABSTRACT

A basketball score-keeping apparatus (10) for detecting and tracking shooting statistics of a player shooting a basketball (12) at a basketball goal (14) that detects a first location at which the basketball (12) crosses a generally horizontal detection plane (26) as it ascends and a second location at which the basketball (12) crosses the detection plane (26) as it descends. The apparatus (10) also tracks the shooting statistics of the player. The apparatus (10) may also include a display (30). The apparatus (10) may be coupled to other similar apparatuses to allow competition between players. Vibration (38) and verification (40) sensors may be part of the apparatus (10) in order to provide additional features.

50 Claims, 2 Drawing Sheets

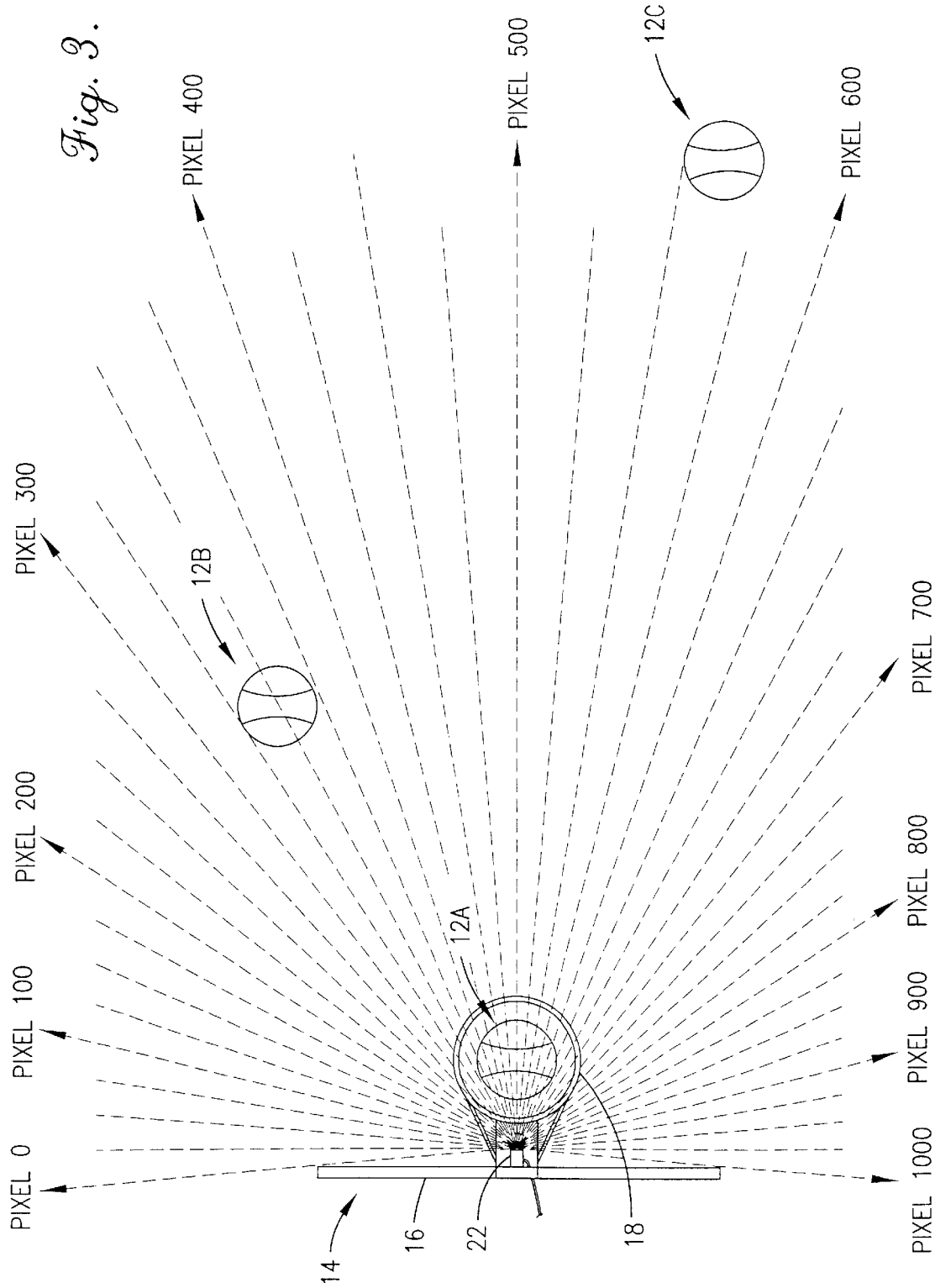

BASKETBALL GOAL SENSOR FOR DETECTING SHOTS ATTEMPTED AND MADE

BACKGROUND OF THE INVENTION

1. Field of the Invention

The present invention relates to an apparatus for detecting and tracking shooting statistics of a basketball player. More particularly, the present invention relates to an apparatus for detecting that a basketball shot was attempted, a location of the attempted shot, and whether the shot was made.

2. Description of the Prior Art

Basketball players often desire to monitor their shooting statistics for recreation, training, or competition purposes. Basketball detecting and tracking devices have been developed for such monitoring; however, these prior art devices are complicated and expensive because they typically use laser beam techniques that require a multitude of laser beams in order to acquire the location of a basketball during play. Furthermore, these prior art devices are inaccurate because they frequently develop false statistics when objects other than basketballs break the paths of the laser beams.

Other prior art devices use accelerometers for detecting whether a basketball shot is made. These devices are also inaccurate because a ball bouncing on a basketball rim could generate false signals. Another inaccuracy in the accelerometer based detection devices is that a made shot may not be detected if the shot did not strike the rim, net, backboard, or any part of the basketball goal system.

Prior art detecting and tracking devices are also limited in that they are designed strictly for gathering shooting statistics at one site only and therefore cannot be used simultaneously by a plurality of players at different sites.

OBJECTS AND SUMMARY OF THE INVENTION

The present invention solves the above-described problems and provides a distinct advance in the art of basketball detecting and tracking devices. More particularly, the present invention provides an apparatus for detecting and tracking shooting statistics for a player that requires the use of only one location detecting device per basketball goal; senses light intensity variation and is thereby able to detect a specific signature of a basketball so as to prevent false detection of objects other than the basketballs; accurately detects whether a shot is made even if the ball bounces on the rim or does not strike the rim before passing through the net; and can connect to other similar apparatuses in order to offer competition between players at different sites.

The apparatus of the present invention broadly includes a detection device for detecting a first location at which a basketball passes through a generally horizontal detection plane as the basketball is launched, for detecting a second location at which the basketball passes through the detection plane as the basketball descends, and for generating output signals representative thereof; and a computing device coupled with and responsive to the detection device for analyzing the output signals and for generating data corresponding to the shooting statistics of the player.

In preferred forms, the detection device is a single machine vision device such as a charge coupled device that senses light intensity variation. The preferred apparatus may also include a display coupled with the computing device for displaying the shooting statistics generated by the computing device and circuitry that couples the apparatus to one or more other similar apparatuses to allow competition between players at different sites.

BRIEF DESCRIPTION OF THE DRAWINGS

FIG. 3 is a top view illustrating a generally horizontal detection plane monitored by the apparatus and the locations of basketballs as they cross the detection plane.

DETAILED DESCRIPTION OF THE PREFERRED EMBODIMENT

Figure 1:
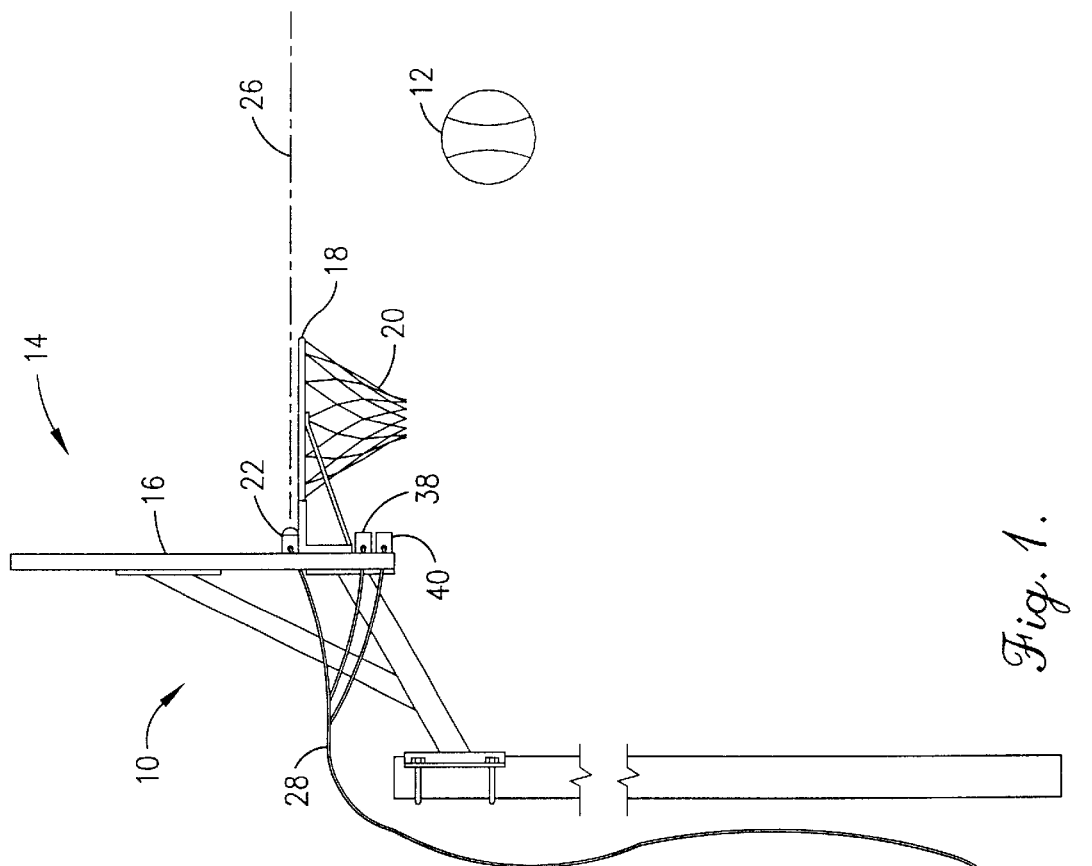
FIG. 1 is a fragmentary side elevational view of a basketball score-keeping apparatus constructed in accordance with a preferred embodiment of the invention.
Figure 2:
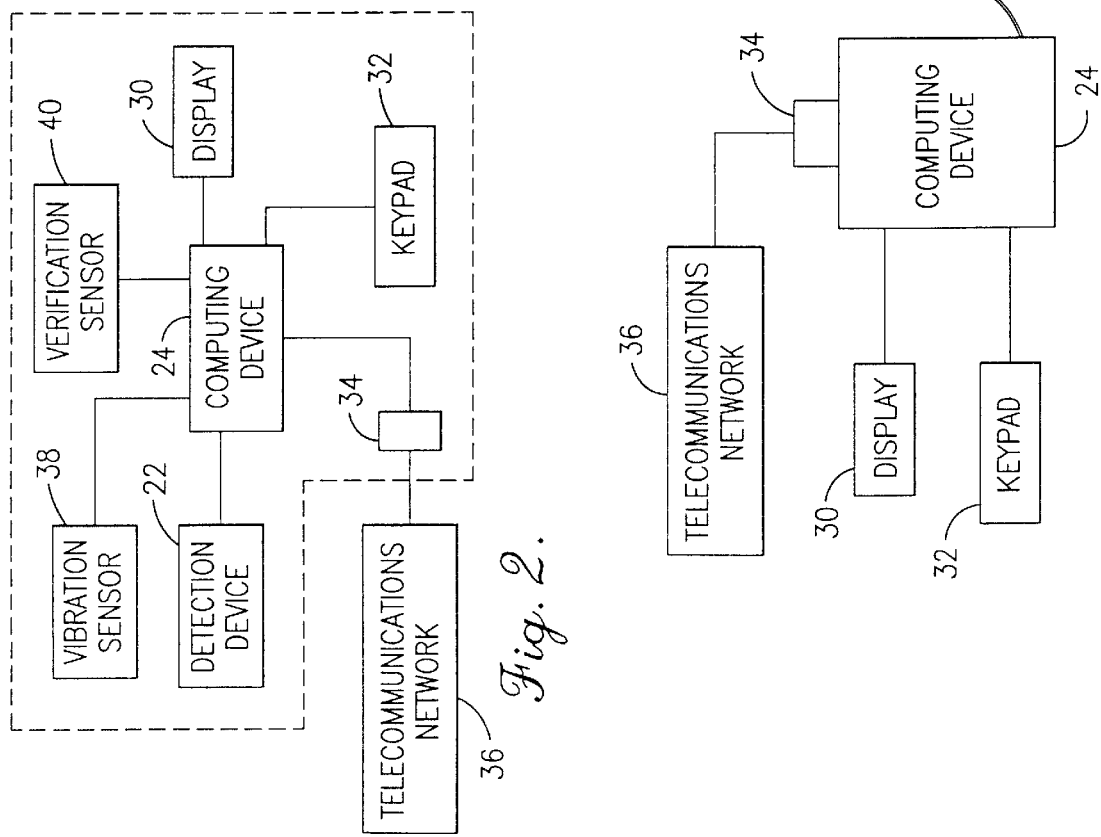
FIG. 2 is a schematic diagram of components of the basketball score-keeping apparatus.

Turning now to the drawing figures and particularly FIG. 1, a basketball score-keeping apparatus generally referred to as numeral 10 constructed in accordance with a preferred embodiment of the invention is illustrated. The score-keeping apparatus 10 is operable to detect and track shooting statistics of one or more players as they shoot a basketball 12 toward a conventional basketball goal 14 including a backboard 16, a rim 18, and a net 20. The shooting statistics may include any statistics related to a basketball game such as a shooting percentage, shots attempted, shots made, field goal percentage, length of time of shooting session, consecutive goals made, three point shots made and locations of shots attempted. The basketball score-keeping apparatus 10 is coupled with an appropriate source of power and broadly includes a detection device 22 and a computing device 24 coupled therewith.

In more detail, the detection device 22 is operable for detecting positional information of the basketball 12 after it has been shot by a player. Specifically, the detection device 22 is operable for detecting a first location at which the basketball 12 passes through a generally horizontal detection plane 26 as it is launched, for detecting a second location at which the basketball 12 passes through the detection plane 26 as it descends, and for generating output signals representative thereof to be sent to the computing device 24. The detection device 22 is preferably configured for mounting to a portion of the basketball goal 14, preferably to or near the rim 18 with conventional brackets or other fasteners so that the detection plane 26 that it monitors extends along an approximately 190 degree arc centered above the rim 18 as depicted in FIG. 3.

In another preferred embodiment, the detection device 22 is operable for monitoring the detection plane 26 for the passages of the basketball 12 and also acts as a motion detector to detect motion above the detection plane 26. The motion detected may include motion caused by the basketball 12 bouncing on the backboard 16 and the rim 18. A quantity of motion, falling in one of a group of precalculated ranges of quantities of motion, above the detection plane 26 indicates that the shot attempt is still in progress.

The detection device 22 is preferably a charge coupled device but may be any machine vision device capable of detecting passage of an object such as the basketball 12 through the detection plane 26. The detection device 22 is preferably a multi-dimensional image sensor; however, a linear image sensor may also be used in embodiments requiring detection only along the horizontal detection plane. A lens may be mounted on the sensor to enhance the detection device's range of vision. Preferably, this lens is a fish eye lens.

The computing device 24 is operably coupled with the detection device 22 by a conventional cable assembly 28 and is responsive to the signals generated by the detection device 22. The computing device 24 is programmed to analyze the signals and to generate data corresponding to the shooting statistics of the player. The computing device 24 is preferably part of an embedded computer system such as the MICRO/SYS PC/104 386EX Computer. The cable assembly 28 may be any device able to transfer signals such as a coaxial cable, a twisted pair of conductors, a multiple wire cable or a wireless coupling.

The computing device 24 is preferably coupled with a display 30 and a keypad 32. The display 30 is for displaying the shooting statistics generated by the computing device 24. The display 30 maybe positioned adjacent the computing device 24 or may be configured for mounting on or near the backboard 16 so that it can be seen during use of the apparatus 10. The display 30 may be any display or monitor such as an LCD display, a touch screen, or any high visibility display.

The keypad 32 is provided for permitting user interactivity with the computing device 24. The keypad 32 may be any input device such as a sixteen-key keypad or a touch screen.

The computing device 24 may also be coupled with a coupling device 34 for connecting the computing device 24 with another similar basketball score-keeping apparatus (not shown). The coupling device 34 includes associated software that enables the computing device 24 to be coupled with another similar apparatus via a telecommunications network 36 or other conventional network such as a landline or wireless telecommunications network, wide area network, local area network, Internet, or intranet or a combination of these networks. Alternatively, two or more score-keeping apparatuses could be coupled together directly via cabling. The coupling device 34 is preferably a conventional male-type telecommunications coupler such as an RJ-11 jack operable for coupling with a corresponding female-type jack coupled to the telecommunications network 36.

In preferred forms, the basketball score-keeping apparatus 10 also includes a vibration sensor 38 and a verification sensor 40. The vibration sensor 38 is coupled to the computing device 24 and configured for mounting to a rigid portion of the basketball goal 14, such as the backboard 16 or the rim 18. The vibration sensor 38 generates a signal and sends it to the computing device 24 when the basketball 12 strikes the backboard 16 or the rim 18 so as to distinguish between a made shot that touches only the net 20 and made shots that first hit the backboard 16 and/or the rim 18. The vibration sensor 38 may be any device that measures movement, vibration or any kind of mechanical shock such as an accelerometer.

The verification sensor 40 verifies that a shot is made. The verification sensor 40 is coupled with the computing device 24 and configured for mounting on the backboard 16 preferably under the rim 18. The verification sensor 40 generates a signal and sends it to the computing device 24 when the basketball 12 passes through the rim 18 so as to verify that a shot has been made. The verification sensor 40 may be any device operable to sense passage of the basketball 12 through the rim 18 such as an ultrasonic sensor, a photoelectric sensor or a mechanical switch assembly.

OPERATION

In operation, the score-keeping apparatus 10 detects and tracks the shooting statistics of one or more players as they shoot the basketball 12 toward the basketball goal 14. When a player first shoots the basketball 12, it ascends and crosses the detection plane 26 monitored by the detection device 22. The detection device 22 responds by sending the signals to the computing device 24 regarding a signature of the basketball 12. Then, as the basketball 12 descends, it again crosses the detection plane 26. The detection device 22 again sends the signals regarding the signature of the basketball 12 to the computing device 24. The computing device 24 receives this information and analyzes it in order to determine a combination of information regarding the distance and the location in reference to the basketball goal 14 that the basketball 12 was launched, and the distance and the location in reference to the basketball goal 14 that the basketball 12 descends. The computing device 24 also determines whether the object detected is the basketball 12 or a different object.

More specifically, the detection device 22 continuously senses the variation in light intensity along the detection plane 26 and sends the signals associated therewith to the computing device 24 for analysis. The computing device 24 processes the signals from the detection device 22, resulting in a digital data stream comprised of individual units of information regarding the graphical image input to the detection device 22. The individual units of information will be referred to as pixels.

The pixels are radially located relative to the detection device 22. When the basketball 12 crosses the detection plane 26 the basketball 12 intersects with a certain quantity and a certain angular location of pixels.

Distance from the basketball goal 14 will be reflected in the quantity of pixels affected. Because of the radial nature of the pixels, the closer to the detection device 22, the more pixels are affected by the basketball 12 crossing through the detection plane 26. The further from the detection device 22, the less quantity of pixels are affected, as the pixels are covering a wider area as the distance from basketball goal 14 increases. The detection device 22 sends the computing device 24 information regarding the quantity of pixels affected.

With regards to angular location, the detection device 22 sends the computing device 24 information regarding the identification of the pixels that are affected by the crossing of the basketball 12 through the detection plane 26. The computing device 24 determines the angular location of the basketball 12 relative to the goal 14 by identifying which of the pixels are affected by the crossing.

The computing device 24 determines the location of the crossing by analyzing the distance from the basketball goal 14 and the angular location of the crossing. The computing device 24 achieves the determination through analyzing the quantity of the pixels affected and which of the pixels were affected.

FIG. 3 illustrates examples of the basketball 12 crossing the detection plane 26, which for these examples has a pattern of 1000 pixels. The number of pixels and other values in this example are for illustrative purposes only and are not to be considered as representing actual values, as actual values may vary. The 1000 pixels are shown in an arc of at least a 190 degree range of vision. The detection device 22 sends the signals to the computing device 24 that includes the quantity of pixels affected and specifically, which of the pixels are affected.

For example, assume that a basketball labeled 12A is shot so that it goes through the rim 18 as depicted. The basketball 12A passing through the rim 18 intersects approximately 300 pixels, numbered between 350 and 650. Therefore, the detection device 22 sends the computing device 24 information that indicates that pixel numbers 350 through 650 are affected when the basketball 12A passes through the rim 18. The computing device 24 receives the signals and determines that the basketball 12A has passed through the rim 18 and therefore the shot was made.

In another example, assume that a basketball labeled 12B passes through the detection plane 26 at a distance of approximately 5 feet from the basketball goal 14. From this distance, approximately 48 of the pixels numbered between 325 and 373 are affected. The detection device 22 therefore sends the computing device 24 this information, which in turn determines the distance and the angular location of the basketball 12B as it passes through the detection plane 26.

As another example, assume that a basketball labeled 12C passes through the detection plane 26 at a distance of 10 feet from the basketball goal 14. In this case, 24 pixels numbered between 550 and 574 are affected. Fewer of the pixels are affected than at the distance of 5 feet because of a radial nature of the detection device 22.

In order to determine whether the object crosses the detection plane 26 and whether the object detected is the basketball 12 or another object, the computing device 24 processes the light intensity measured by each pixel. The computing device 24 matches the light intensity with a numerical value. For example, the light intensity could vary from 0 (darkest) to 256 (brightest) for every pixel. The computing device 24 analyzes the levels of ambient light at the detection plane 26.

Many procedures can be implemented to analyze ambient light and take the ambient light into account when determining the detection of a signature of the object. The preferred method includes the computing device 24 analyzing the ambient light by shifting samples from the detection plane 26 into a memory in the computing device 24, making a copy of the samples, assigning a negative value to the copies, adding together the samples from the detection plane 26 and the copies with the negative values to give a null horizontal line that consists of zeros at times of no basketball detection.

When the basketball 12 crosses the detection plane 26, a group of values representing the pixels affected at the location of the basketball 12 passing through the detection plane 26 changes and the computing device 24 detects the change. The computing device 24 retains the ambient light level and can thereby recall it at system startup. Variations in the levels of ambient light indicate that an object has crossed the detection plane 26.

When the computing device 24 senses variations in the levels of ambient light, it compares the variations in the levels of ambient light to the known signature of the basketball 12. Through this comparison, the computing device 24 determines from the variation in light intensity if the object passing through the detection plane 26 is the basketball 12.

A distinct shape of the basketball 12 creates a specific signature as it crosses through the detection plane 26. If, for example, the detection device 22 is a linear machine vision device, the detection device 22 reads one horizontal layer at a time. If, for example, the basketball 12 ascends through the detection plane 26, the basketball 12 enters the detection plane 26 with a rounded top. As the basketball 12 further enters the detection plane 26, it presents a wider view of the midsection of the basketball 12. The last view of the basketball 12 is the other round area of the basketball 12 as it exits the detection plane 26. These pieces of information create the signature of the basketball 12.

The signature of a basketball 12 contrasts with a signature of a hand entering the detection plane 26. The hand entering the detection plane 26 has a continuously detected area at the end of the entry into the detection plane 26, as the hand is attached to a person and generally retracts back through the detection plane 26, thereby producing a different signature than the signature of the basketball 12.

The computing device 24 registers the signature of the basketball 12 as the object whose light intensity will be of a changing value as the basketball 12 enters the detection plane 26. The light intensity will then change again after the basketball 12 has passed through the detection plane 26. The computing device 24 will determine the distance between the basketball 12 and the basketball goal 14 through analyzing the width of the changed intensity pixel group as the basketball 12 passes through the detection plane 26. The computing device 24 may be programmed with the signature of the basketball 12 so that other objects such as the hand will not be taken into account as the basketball 12.

In another preferred embodiment, the detection device 22 monitors the detection plane 26 for the passages of the basketball 12 and also detects for the motion above the detection plane 26. The detection device 22 sends light intensity information to the computing device 24. The computing device 24 analyzes the light intensity information from each of a plurality of horizontal lines (not shown) angularly spaced above the basketball goal 14.

The quantity of the horizontal lines may vary. For example purposes only, the horizontal lines may number a total of 500 from a line projected directly upward from the detection device 22 to a line projected directly downwards from the detection device 22. For this example, the horizontal lines would extend from a position 1, projected directly upward from the detection device 22 to a position 250, which coincides with the position of the generally horizontal detection plane 26, to a position 500 which projects directly downward from the detection device 22.

To monitor for the motion above the detection plane 26, the computing device 24 performs an ambient light analysis on the information received from the horizontal lines 1 through 249 by processing the light intensity measured by each pixel in each horizontal line. The computing device 24 matches the light intensity with a numerical value. For example, the light intensity could vary from 0 (darkest) to 256 (brightest) for every pixel.

As described above, many procedures can be implemented to analyze ambient light and take the ambient light into account when determining the detection of motion above the detection plane 26. The preferred method includes the computing device 24 analyzing the ambient light by shifting samples from the horizontal lines 1 through 249 into a memory in the computing device 24, making a copy of the samples, assigning a negative value to the copies, adding together the samples from the horizontal lines I through 249 and the copies with the negative values to give a null background that consists of zeros at times of no motion detection above detection plane 26. The computing device 24 retains the ambient light level and can thereby recall it at system startup, and after each completed shot attempt.

When the basketball 12 enters the area above the detection plane 26, the computing device 24 continues to measure a change in the light intensity. The computing device 24 sums the total change in the light intensity that occurs in the area above the detection plane 26 throughout the shot attempt. For example, when the basketball 12 bounces on the backboard 16 and the rim 18, the computing device 24 sums total variation in light intensity in the area above the detection plane 26 throughout the shot attempt.

A particular amount of motion will correspond to a range of light intensity variation. The computing device 24 contains precalculated stored ranges of values corresponding to types of motion.

The computing device 24 compares the sum of the total variation in light intensity to the stored values throughout the shot attempt. Through this comparison, the computing device 24 determines the activity of the basketball 12 while the basketball 12 is above the detection plane 26. For example, the total variations in the light intensity may correspond to a precalculated stored range in the computing device 24 that indicates that the basketball 12 is bouncing on the backboard 16 and rim 18. A different predetermined value for the total variation in light intensity will determine that the basketball 12 may be ascending through the area above the detection plane 26 without encumbrance.

While the foregoing measurements of the total variation in light intensity is taken in the area above the detection plane 26, it is readily apparent to one skilled in the art that the computing device 24 could perform the monitoring of motion above the detection plane 26 by other apparent methods, such as monitoring variation in light intensity in every horizontal line or in every pixel rather than in the entire area above the detection plane 26.

The vibration sensor 38 registers a signal when the basketball 12 strikes the backboard 16 or the rim 18. The computing device 24 receives the signal from the vibration sensor 38. The computing device 24 analyzes the signal in combination with the output signals from the detection device 22 to determine if a basketball shot was successful without striking the backboard 16 or the rim 18. This information may be used in calculating the shooting statistics.

The verification sensor 40 detects whether the basketball 12 passes through the rim 18. From the location under the rim 18, the verification sensor 40 senses the passage of the basketball 12 through the rim 18. For example, if the verification sensor 40 is the mechanical switch assembly, the basketball 12 will contact a mechanical arm which will deflect. Upon deflection, the mechanical switch assembly sends a verification signal to the computing device 24 that the basketball shot was successful.

The computing device 24 also tracks the shooting statistics of the player. In the preferred embodiment, the computing device 24 increases a shot counter by one for each time that the basketball 12 ascends through the detection plane 26. The computing device 24 also increments a field goal counter by one for each time an attempted shot goes though the basketball goal 14. In the event that the basketball 12 does not pass through the basketball goal 14, the computing device 24 counts the basketball 12 as a missed shot.

The computing device 24 may also assign section counters to individual sections of a basketball court. The computing device 24 increments the section counter corresponding to a particular section of the basketball court by one when the basketball 12 ascends through the detection plane 26 from that section of the basketball court.

The computing device 24 also preferably monitors for a passage of an amount of time for a basketball playing session in order to analyze a time period over which the shooting statistics are kept. From the time period information and the foregoing shot information, the computing device 24 processes the shooting statistics. The shooting statistics may be shown on the display 30.

The statistical data may be used in computer programs that include the capability of timed games. The computer programs may accumulate points based on field goals made, consecutive goals made, field goal percentage and other applicable basketball playing information.

The telecommunications network 36 or other conventional network connections provide the player with an ability to play with other players. The play may be on a stored or a real time basis. Preferably, the player will compete with other players by the timed games via the Internet network on the real time basis.

Although the invention has been described with reference to the preferred embodiment illustrated in the attached drawing figures, it is noted that equivalents may be employed and substitutions made herein without departing from the scope of the invention as recited in the claims. For example, although the apparatus 10 is drawn with the cable assembly 28 shown between the detection device 22 and the computing device 24, a wireless transmission of the detection device signals may be used.

Having thus described the preferred embodiment of the invention, what is claimed as new and desired to be protected by letters patent includes the following:

What is claimed is:

1. A basketball score-keeping apparatus for detecting and tracking shooting statistics of a player shooting a basketball at a basketball goal comprising:

a detection device for detecting a first location at which the basketball passes through a generally horizontal detection plane as the basketball is launched, for detecting a second location at which the basketball passes through the generally horizontal detection plane as the basketball descends, and for generating output signals representative thereof; and a computing device coupled with and responsive to the detection device for analyzing the output signals and for generating data corresponding to the shooting statistics of the player, wherein the computing device is configured for analyzing levels of ambient light at the generally horizontal detection plane.

2. A basketball score-keeping apparatus as recited in claim 1, further comprising a display coupled with the computing device for displaying the shooting statistics generated by the computing device.

3. A basketball score-keeping apparatus as recited in claim 1, wherein the detection device is a charge coupled device.

4. A basketball score-keeping apparatus as recited in claim 1, wherein the detection device is configured for mounting to a portion of the basketball goal.

5. A basketball score-keeping apparatus as recited in claim 4, wherein the portion of the basketball goal is a rim of the basketball goal.

6. A basketball score-keeping apparatus as recited in claim 1, wherein the computing device is configured to analyze a time period over which the shooting statistics are kept.

7. A basketball score-keeping apparatus as recited in claim 6, wherein the computing device is configured to use the time period to process the shooting statistics.

8. A basketball score-keeping apparatus as recited in claim 7, further comprising a coupling device for connecting the computing device with a second basketball score-keeping apparatus.

9. A basketball score-keeping apparatus as recited in claim 8, wherein the coupling device includes a coupling to a telecommunications network.

10. A basketball score-keeping apparatus as recited in claim 1, further comprising a vibration sensor for detecting whether the basketball strikes a rigid portion of the basketball goal.

11. A basketball score-keeping apparatus as recited in claim 10, wherein the vibration sensor is an accelerometer.

12. A basketball score-keeping apparatus as recited in claim 1, further comprising a verification sensor for detecting whether the basketball passes through a rim of the basketball goal.

13. A basketball score-keeping apparatus as recited in claim 12, wherein the verification sensor is selected from the group consisting of an ultrasonic sensor, a photoelectric sensor, and a mechanical switch assembly.

14. A basketball score-keeping apparatus as recited in claim 1, wherein the shooting statistics are selected from the group consisting of shooting percentage, shots attempted, shots made, field goal percentage, length of time of shooting session, consecutive goals made, three point shots made and locations of shots attempted.

15. A basketball score-keeping apparatus as recited in claim 1, wherein the computing device is configured for analyzing variations in the levels of ambient light.

16. A basketball score-keeping apparatus as recited in claim 15, wherein the computing device is configured for comparing the variations in the levels of ambient light to a signature of the basketball to determine if an object passing through the generally horizontal detection plane is the basketball.

17. A basketball score-keeping apparatus for detecting and tracking shooting statistics of a player shooting a basketball at a basketball goal comprising:

a machine vision device for detecting a first location at which the basketball passes through a generally horizontal detection plane as the basketball is launched, for detecting a second location at which the basketball passes through the generally horizontal detection plane as the basketball descends, and for generating output signals representative thereof;

a computing device coupled with and responsive to the machine vision device for analyzing the output signals and for generating data corresponding to the shooting statistics of the player; and a display coupled with the computing device for displaying the shooting statistics generated by the computing device, wherein the computing device is configured for analyzing levels of ambient light at the generally horizontal detection plane.

18. A basketball score-keeping apparatus as recited in claim 17, wherein the machine vision device is a charge coupled device.

19. A basketball score-keeping apparatus as recited in claim 17, wherein the machine vision device is configured for mounting to a portion of the basketball goal.

20. A basketball score-keeping apparatus as recited in claim 19, wherein the portion of the basketball goal is a rim of the basketball goal.

21. A basketball score-keeping apparatus as recited in claim 17, wherein the computing device is configured to analyze a time period over which the shooting statistics are kept.

22. A basketball score-keeping apparatus as recited in claim 21, wherein the computing device is configured to use the time period to process the shooting statistics.

23. A basketball score-keeping apparatus as recited in claim 22, further comprising a coupling device for connecting the computing device with a second basketball score-keeping apparatus.

24. A basketball score-keeping apparatus as recited in claim 23, wherein the coupling device includes a coupling to a telecommunications network.

25. A basketball score-keeping apparatus as recited in claim 17, further comprising a vibration sensor for detecting whether the basketball strikes a rigid portion of the basketball goal.

26. A basketball score-keeping apparatus as recited in claim 25, wherein the vibration sensor is an accelerometer.

27. A basketball score-keeping apparatus as recited in claim 17, further comprising a verification sensor for detecting whether the basketball passes through a rim of the basketball goal.

28. A basketball score-keeping apparatus as recited in claim 27, wherein the verification sensor is selected from the group consisting of an ultrasonic sensor, a photoelectric sensor, and a mechanical switch assembly.

29. A basketball score-keeping apparatus as recited in claim 17, wherein the shooting statistics are selected from the group consisting of shooting percentage, shots attempted, shots made, field goal percentage, length of time of shooting session, consecutive goals made, three point shots made and locations of shots attempted.

30. A basketball score-keeping apparatus as recited in claim 17, wherein the computing device is configured for analyzing variations in the levels of ambient light.

31. A basketball score-keeping apparatus as recited in claim 30, wherein the computing device is configured for comparing the variations in the levels of ambient light to a signature of the basketball to determine if an object passing through the generally horizontal detection plane is the basketball.

32. A basketball score-keeping apparatus for detecting and tracking shooting statistics of a player shooting a basketball at a basketball goal comprising:

a detection device for detecting a first location at which the basketball passes through a generally horizontal detection plane as the basketball is launched, for detecting a second location at which the basketball passes through the generally horizontal detection plane as the basketball descends, for detecting motion above the generally horizontal detection plane, and for generating output signals representative thereof; and a computing device coupled with and responsive to the detection device for analyzing the output signals and for generating data corresponding to the shooting statistics of the player, wherein the computing device is configured for analyzing levels of ambient light at the generally horizontal detection plane.

33. A basketball score-keeping apparatus as recited in claim 32, further comprising a display coupled with the computing device for displaying the shooting statistics generated by the computing device.

34. A basketball score-keeping apparatus as recited in claim 32, wherein the detection device is a charge coupled device.

35. A basketball score-keeping apparatus as recited in claim 32, wherein the detection device is configured for mounting to a portion of the basketball goal.

36. A basketball score-keeping apparatus as recited in claim 35, wherein the portion of the basketball goal is a rim of the basketball goal.

37. A basketball score-keeping apparatus as recited in claim 32, wherein the computing device is configured to analyze a time period over which the shooting statistics are kept.

38. A basketball score-keeping apparatus as recited in claim 37, wherein the computing device is configured to use the time period to process the shooting statistics.

39. A basketball score-keeping apparatus as recited in claim 38, further comprising a coupling device for connecting the computing device with a second basketball score-keeping apparatus.

40. A basketball score-keeping apparatus as recited in claim 39, wherein the coupling device includes a coupling to a telecommunications network.

41. A basketball score-keeping apparatus as recited in claim 32, further comprising a vibration sensor for detecting whether the basketball strikes a rigid portion of the basketball goal.

42. A basketball score-keeping apparatus as recited in claim 41, wherein the vibration sensor is an accelerometer.

43. A basketball score-keeping apparatus as recited in claim 32, further comprising a verification sensor for detecting whether the basketball passes through a rim of the basketball goal.

44. A basketball score-keeping apparatus as recited in claim 43, wherein the verification sensor is selected from the group consisting of an ultrasonic sensor, a photoelectric sensor, and a mechanical switch assembly.

45. A basketball score-keeping apparatus as recited in claim 32, wherein the shooting statistics are selected from the group consisting of shooting percentage, shots attempted, shots made, field goal percentage, length of time of shooting session, consecutive goals made, three point shots made and locations of shots attempted.

46. A basketball score-keeping apparatus as recited in claim 32, wherein the computing device is configured for analyzing variations in the levels of ambient light.

47. A basketball score-keeping apparatus as recited in claim 46, wherein the computing device is configured for comparing the variations in the levels of ambient light to a signature of the basketball to determine if an object passing through the generally horizontal detection plane is the basketball.

48. A basketball score-keeping apparatus for detecting and tracking shooting statistics of a player shooting a basketball at a basketball goal comprising:
   a detection device for detecting a first location at which the basketball passes through a generally horizontal detection plane as the basketball is launched, for detecting a second location at which the basketball passes through the generally horizontal detection plane as the basketball descends, for detecting motion above the generally horizontal detection plane, and for generating output signals representative thereof; and
   a computing device coupled with and responsive to the detection device for analyzing the output signals and for generating data corresponding to the shooting statistics of the player,
   wherein the computing device is configured for analyzing levels of ambient light in an area above the generally horizontal detection plane.

49. A basketball score-keeping apparatus as recited in claim 48, wherein the computing device is configured for analyzing variations in the levels of ambient light.

50. A basketball score-keeping apparatus as recited in claim 49, wherein the computing device is configured for comparing the variations in the levels of ambient light to ranges of values to determine a type of motion that has occurred in the area above the generally horizontal detection plane.

* * * * *